(12) United States Patent
Hackstein et al.

(10) Patent No.: US 9,958,401 B2
(45) Date of Patent: May 1, 2018

(54) METHOD AND DEVICE FOR DETERMINING AT LEAST ONE CONCENTRATION OF COAL PARTICLES IN A GAS FLOW

(71) Applicant: SIEMENS AKTIENGESELLSCHAFT, München (DE)

(72) Inventors: Holger Hackstein, Dietzenbach (DE); Christian Morhart, München (DE); Dominikus Joachim Müller, Eichenau (DE); Florian Poprawa, München (DE); Andreas Ziroff, München (DE)

(73) Assignee: Siemens Aktiengesellschaft, München (DE)

( * ) Notice: Subject to any disclaimer, the term of this patent is extended or adjusted under 35 U.S.C. 154(b) by 58 days.

(21) Appl. No.: 14/780,436

(22) PCT Filed: Mar. 24, 2014

(86) PCT No.: PCT/EP2014/055817
§ 371 (c)(1),
(2) Date: Sep. 25, 2015

(87) PCT Pub. No.: WO2014/154622
PCT Pub. Date: Oct. 2, 2014

(65) Prior Publication Data
US 2016/0069822 A1    Mar. 10, 2016

(30) Foreign Application Priority Data
Mar. 27, 2013 (DE) .................. 10 2013 205 478

(51) Int. Cl.
*G01N 22/00* (2006.01)
*G01F 1/74* (2006.01)
(Continued)

(52) U.S. Cl.
CPC ............. *G01N 22/00* (2013.01); *G01N 15/06* (2013.01); *G01F 1/74* (2013.01); *G01N 2015/0046* (2013.01); *G01N 2015/0693* (2013.01)

(58) Field of Classification Search
CPC .. G01F 1/663; G01F 1/74; G01F 1/66; G01N 21/53; G01N 22/00; G01N 15/06;
(Continued)

(56) References Cited

U.S. PATENT DOCUMENTS

| 4,598,593 | A |   | 7/1986 | Sheen et al. |
| 5,535,747 | A | * | 7/1996 | Katakura ................. A61B 8/06 600/438 |

(Continued)

FOREIGN PATENT DOCUMENTS

| CN | 2323270 Y | 6/1999 |
| CN | 101082559 A | 12/2007 |

(Continued)

OTHER PUBLICATIONS

Buchan P.B. et al: A radar-Doppler autocorrelation analysis of insect activity, Physiological Entomology, Bd. 4, Nr. 2, pp. 103-109, ISSN: 0307-6962, DOI: 10.1111/j.1365-3032-1979-tb00184.x, XP055117280, 1979.
(Continued)

*Primary Examiner* — Randy Gibson
*Assistant Examiner* — Gedeon M Kidanu
(74) *Attorney, Agent, or Firm* — Lempia Summerfield Katz LLC

(57) ABSTRACT

The present embodiments relate to a device and a method for determining at least one concentration of coal particles in a gas flow flowing through a channel, wherein at least part of the gas flow having coal particles contained therein is measured by at least one microwave sensor and at least one
(Continued)

measurement signal characterizing the concentration of the coal particles is provided, wherein an autocorrelation function of the measurement signal is determined and at least one distance value characterizing a distance of a point of the gas flow belonging to the concentration from the microwave sensor is determined in dependence on the autocorrelation function.

16 Claims, 1 Drawing Sheet

(51) Int. Cl.
*G01N 15/06* (2006.01)
*G01N 15/00* (2006.01)

(58) Field of Classification Search
CPC ... G01N 2015/0046; G01N 2015/0693; G01N 15/0656; G01N 15/1031; G01N 2015/0026; G01N 2015/0053; G01S 13/583; G01S 2013/466
USPC ..................................... 73/24.03; 250/356.1
See application file for complete search history.

(56) References Cited

U.S. PATENT DOCUMENTS

| | | | | |
|---|---|---|---|---|
| 5,600,073 | A * | 2/1997 | Hill | G01B 5/28 73/30.03 |
| 7,102,133 | B2 * | 9/2006 | Happel | G01F 1/663 250/356.1 |
| 7,310,046 | B2 * | 12/2007 | Young | G01F 1/663 340/606 |
| 7,852,091 | B2 * | 12/2010 | Sinha | F16L 55/48 324/637 |
| 2003/0066358 | A1 * | 4/2003 | King | G01F 1/663 73/861.11 |
| 2005/0001169 | A1 * | 1/2005 | Happel | G01F 1/663 250/356.1 |
| 2014/0331980 | A1 * | 11/2014 | Engstrom | G01F 1/86 123/672 |
| 2016/0003728 | A1 * | 1/2016 | Hardalupas | G01N 15/1434 356/336 |

FOREIGN PATENT DOCUMENTS

| | | |
|---|---|---|
| CN | 101344493 A | 1/2009 |
| CN | 201311388 Y | 9/2009 |
| CN | 202024793 U | 11/2011 |
| DE | 4426280 A1 | 2/1996 |
| EP | 0916929 A1 | 5/1999 |
| WO | WO03012375 A2 | 2/2003 |

OTHER PUBLICATIONS

PCT International Search Report and Written Opinion of the International Searching Authority dated May 22, 2014 for corresponding PCT/EP2014/055817.

Penirschke A. et al: Microwave Mass Flow Sensor for Process Monitoring Applications, Microwave symposium digest, 2008 IEEE MTT-S International, IEEE, pp. 1195-1198, ISBN: 978-1-4244-1780-3, XP031465221, 2008.

Chinese Office Action for related Chinese Application No. 2014 800 184 64.3 dated Jul. 10, 2017.

* cited by examiner

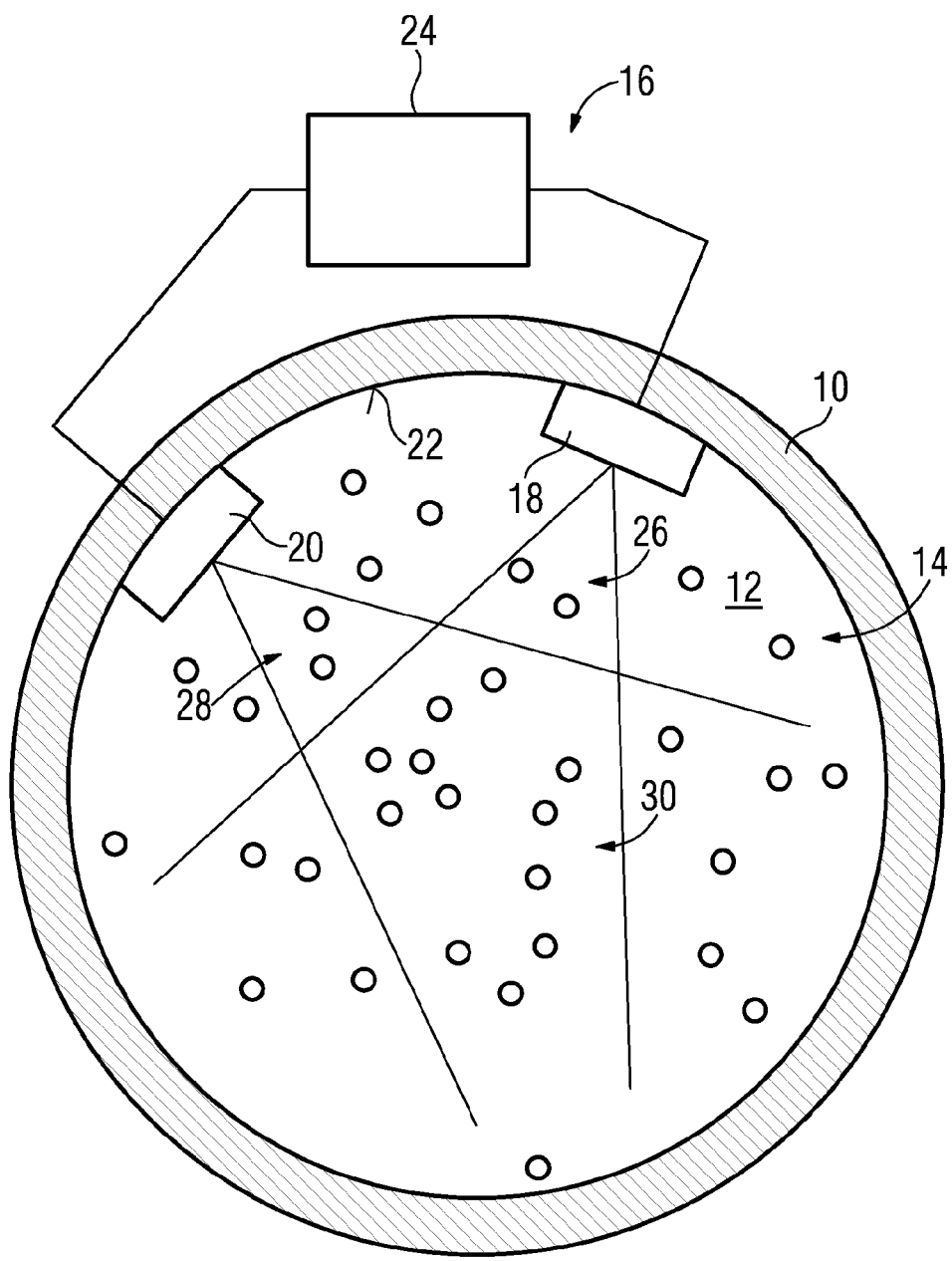

METHOD AND DEVICE FOR DETERMINING AT LEAST ONE CONCENTRATION OF COAL PARTICLES IN A GAS FLOW

CROSS-REFERENCE TO RELATED APPLICATIONS

The present patent document claims the benefit of DE 102013205478.5, filed on Mar. 27, 2013, and PCT/EP2014/055817, filed on Mar. 24, 2014 which are hereby incorporated by reference.

TECHNICAL FIELD

The present embodiments relate methods and devices for determining the concentration of coal particles in a gas flow.

BACKGROUND

By way of example, a method and device may be used, in the case of internal combustion engines and combustion systems for power generation, for monitoring and keeping a check on a combustion process in the internal combustion engine or in the combustion system. As part of the combustion process, coal particles are burned in at least one combustion chamber. To realize an optimized combustion process, or a combustion process that may be advantageous with regard to the occurrence of pollutants, the homogeneity of the mass concentration of the coal particles that are fed to the combustion chamber over time may play an important part.

The coal particles are fed to the combustion chamber (e.g., by a gas flow, in particular an air flow in which the coal particles are taken up). Inhomogeneities of the mass concentration in the gas flow may occur due to different mechanical and flow-dynamic effects (e.g., manifested as increased concentrations of dust of the coal particles locally within a flow pipe of the gas flow). Such inhomogeneities with regard to the distribution of the mass concentration of the coal particles in the gas flow are undesired and should be detected, so that as a consequence countermeasures may be taken (e.g., to avoid such inhomogeneities).

SUMMARY AND DESCRIPTION

An object of the present embodiments is to provide a method and a device for determining at least one concentration of coal particles in a gas flow by inhomogeneities of the distribution or the concentration distribution of the coal particles at least in part of the gas flow that may be recorded in a particularly easy way.

A first aspect of the present embodiments concerns a method for determining at least one concentration of coal particles in a gas flow flowing through a channel. In the method, at least part of the gas flow with coal particles taken up therein is recorded by at least one microwave sensor. Furthermore, at least one measurement signal characterizing the concentration of the coal particles is provided by the microwave sensor.

As part of the method, an autocorrelation function of the measurement signal is determined. Furthermore, at least one distance value characterizing a distance of a point of the gas flow associated with the concentration from the microwave sensor is determined in dependence on the autocorrelation function BUCHAN, P. B. et al.: A radar-Doppler autocorrelation analysis of insect activity. Physiological Entomology, Bd. 4, Nr. 2, pp. 103-109, ISSN: 0307-6962, 1979 defines an autocorrelation function as providing "a measure of the similarity of the signal to a time-delayed version of itself" and provides an example equation for deriving the function. (BUCHAN, P. B. et al., pp. 104-105).

In other words, at least one concentration of coal particles in the gas flow is determined based on the measurement signal. This concentration is present at a point of the gas flow or in the gas flow. This point or position in relation to the gas flow (e.g., in relation to the microwave sensor) is not being determined, is not possible to be determined, or is only able to be determined with very great effort. In order therefore to assign the at least one concentration of the point in the gas flow in relation to the microwave sensor, the autocorrelation function of the measurement signal is determined and the distance value is determined in dependence on the autocorrelation function. It is thus possible as part of the method to determine in a way that is particularly easy, and consequently involves little time and cost, the position of the point at which the at least one concentration is present in relation to the microwave sensor, and consequently in relation to the gas flow. As a consequence, it is possible to draw conclusions in a particularly easy way concerning the concentration distribution of the coal particles (e.g., at least in the part of the gas flow). The position of the point at which the at least one concentration is present is characterized in this case by the distance value (e.g., by the distance of the point from the microwave sensor). Since the position of the microwave sensor in relation to the channel or in relation to the gas flow is known, the position of the point at which the at least one concentration is present in relation to the channel or the gas flow may also be calculated from the distance value in an altogether easy way.

It is provided that a number of concentrations or associated concentration values of the coal particles in the gas flow may be recorded or determined based on the measurement signal, and that it is possible by the determination of the autocorrelation function of the measurement signal to determine respective distances or distance values of respective points at which the respective concentrations are present from the microwave sensor. In this way it is possible to determine the concentration distribution of the coal particles in the gas flow, to record any inhomogeneities of the concentration distribution, and to record the distribution of the coal particles overall.

Such an inhomogeneity of the concentration distribution exists if, for example, it is determined that a first concentration of the coal particles is present at a first point while a second concentration of the coal particles is present at a second point at a distance from the first point, and while the second concentration at the second point is much greater than the first concentration at the first point. If such an inhomogeneity of the concentration distribution is recorded, corresponding countermeasures may be initiated in order to avoid such undesired inhomogeneities. For example, it is possible to influence the gas flow with regard to how it flows (e.g., in order to bring about an at least substantially homogeneous distribution of the coal particles in the gas flow).

It is consequently possible by the method to record the concentration of the coal particles. In addition, a spatial resolving capability may be created in an easy way, so that the point at which the concentration is present, or its position in relation to the gas flow, can also be determined. No complex additional sensors are required or provided for this purpose. Rather, data from reflection and transmission measurements carried out by the at least one microwave sensor may be used.

The present embodiments are based on finding that numerous individual coal dust particles that have a series of statistical properties are taken up in the gas flow (e.g., an air flow). For example, the statistical properties are the grain size or the particle size, the grain distribution or the particle distribution, the particle shape, particle material properties (e.g., such as ash content and/or moisture, etc.), the particle position at a given point in time and the particle velocity.

Although the coal particles can only be individually detected in the measurement signal in exceptional cases (e.g., because their size and reflectivity are too small), the totality of the coal particles may be observed in the measurement signal. The corresponding measurement signal consequently carries numerous properties of statistical noise. These statistical properties carry additional items of information, however, the evaluation of the additional information is possible and may be performed as part of the method by the determination of the autocorrelation function.

The method is also based on the idea that an individual coal particle, although it is not detectable as such in the statistical measurement signal, may provide a contribution to the measurement signal that may be regarded as deterministic, if the trajectory and reflectivity of the coal particle are known. Under these circumstances, the contribution to the signal of this individual coal particle has an autocorrelation function that is different from zero for as long as the time the coal particle is recorded by the microwave sensor. In other words, the autocorrelation function of the individual coal particle is different from zero for as long as the coal particle is in the recording area of the microwave sensor, or as long as the transit of the coal particle through the field of view or the recording area of the microwave sensor lasts.

Additionally, on account of what is known as the beam spread of the microwave signal emitted by the microwave sensor, coal particles that are far away from the microwave sensor require correspondingly longer to pass through the recording area of the microwave sensor than coal particles that are comparatively closer to the microwave sensor passing through its recording area. Therefore, the coal particles that are farther away from the microwave sensor and are passing through the recording area have an autocorrelation function that is more prolonged in temporal terms than the coal particles that are closer to the microwave sensor passing through its recording area.

This property of the individual coal particle is transferred to the autocorrelation function of the actual scenario or measurement signal that is composed by superposing the multiplicity of coal particles. While the directly measured items of information of the microwave sensor have a character similar to noise, it is found that streaks of coal particles that pass very close to or directly in front of the microwave sensor have a relatively short autocorrelation function in terms of time, while streaks of coal particles that are further away from the microwave sensor in comparison have an autocorrelation function that is more prolonged (e.g., over a longer time).

Based on these findings, it is possible by the autocorrelation function to record streaks of coal particles that are different distances away from the microwave sensor and the concentration. In this way, any inhomogeneities with regard to the concentration of the coal particles in the gas flow may be recorded.

To realize a particularly low-cost way of carrying out the method, in one embodiment the microwave sensor is operated with one frequency. Operating with one frequency allows the method to be carried out with a particularly simple, low-cost microwave sensor (e.g., preferably operated in at least substantially continuous, single-frequency operation). For example, a Doppler sensor may be used as the microwave sensor.

In another embodiment, at least one position value that characterizes a position of the point in relation to the channel is determined in dependence on the distance value. It is thereby possible, based on the distance value, to determine the position of the point at which the at least one concentration is present in relation to the channel or in relation to the gas flow overall. This allows the concentration distributions or any inhomogeneities of the concentration distribution to be determined particularly precisely.

In a further embodiment, using at least a second microwave sensor, at least the part of the gas flow with the coal particles taken up therein is recorded, and at least a second measurement signal characterizing the concentration of the coal particles is provided. Furthermore, a second autocorrelation function of the second measurement signal is determined. In addition, at least a second distance value, characterizing a distance of the point of the gas flow associated with the concentration from the second microwave sensor, is determined in dependence on the determined second autocorrelation function.

It is possible using the second sensor to calculate the second distance value and to compare the second distance value with the first distance value. This allows for compensation of any measuring errors. As a consequence, it is possible to record the concentration distribution of the coal particles in the gas flow precisely. By corresponding use and arrangement of a number of microwave sensors (e.g., along a circumference of a pipe bounding the channel), a number of items of sensor information may be obtained from at least partially overlapping measuring zones. In other words, respective recording areas of the microwave sensors may overlap.

It is possible to record the overlapping area both by the first sensor and by the second sensor, to determine corresponding data over the overlapping area and to compare the corresponding data (e.g., to compensate for measuring errors). By suitable calculation of the individual items of sensor information, tomographically acting evaluation methods may be provided. As a result, it is possible to increase the reliability and meaningfulness of the concentration or density distribution obtained within the channel.

By using microwave sensors of which the microwave sources are operated with a known frequency and phase relationships with respect to one another, moreover the items of transmission information between the microwave sensors may be evaluated. If, for example, a coal particle is impinged by a signal emitted by the first microwave sensor (e.g., microwaves), such that the signal is scattered (e.g., so that scattered signals are produced), and such that the scattered signals reach a second microwave sensor and/or third microwave sensor (e.g., different from the first microwave sensor), and the scattered signals may be recorded by the second and/or third sensor. The information content of the overall measurement that may be used for the evaluation increases in comparison with the use of just one sensor.

In an embodiment, it is provided that the position value is determined in dependence on the distance values. In other words, both distance values are taken into consideration for the determination of the position value, such that the position value may be calculated particularly accurately.

It is also possible for signal evaluation to determine a cross-correlation function of the measurement signals of the microwave sensors. In other words, it is possible to calculate and evaluate cross correlations between the microwave sensors. For example, with the aid of cross correlations or cross-correlation functions, an imaging method of measuring the cross section of the channel may be provided. For this purpose two rows with respective microwave sensors that direct measurements into the same volume of the gas flow at an angle in relation to one another may be provided in a respectively linear arrangement. In other words, the microwave sensors are aligned in relation to one another such that respective center axes of respective measuring areas of the microwave sensors form an included angle with one another, and the measuring areas are able to cover the area of the gas flow that is common to the microwave sensors.

If the cross correlations of the microwave sensors from a first of the rows and a second row are investigated, it can be established that (e.g., in the presence of a streak in the overlapping area of the respective recording areas of the microwave sensors) the cross correlations or the cross-correlation functions assume a value different from zero, whereas the other cross correlations are at least substantially zero. Thus, it is possible to localize the position of the streaks of coal particles, and consequently their concentration or density, exactly in order to record any inhomogeneities particularly well.

The evaluation of the cross correlations is also possible whenever the microwave sensors or their respective center axes are not arranged at right angles or as a linear arrangement but for example are mounted on the circumference of a pipe bounding the channel. An important factor for this type of evaluation is a suitably provided coincidence or overlap of the respective recording areas of the microwave sensors. The recording areas also being referred to as fields of view of the microwave sensors.

An advantage of the cross-correlation-based evaluation may be that cross-correlation-based evaluation does not require that the microwave sensors have to be coherently operated or that the relative position of respective frequencies of the microwave sensors has to be known. The method may consequently be carried out particularly easily.

By using the information about the position of the at least one concentration, the measurement signal (e.g., a mass flow signal), may be assessed in such a way that a mass flow measuring error attributable to the presence of the streaks of coal particles may be corrected or compensated.

As part of the method, statistical properties of the at least one measurement signal are evaluated to determine the distance (e.g., radial distance) of the at least one concentration from the microwave sensor. One advantage of determining the distance is that in this way a distance resolution of microwave sensors may be easily realized. By contrast with frequency-modulated continuous-wave (FMCW) or pulsed methods, the distance resolution may be realized with only little expenditure on circuitry and only little expenditure on systems engineering.

However, it is quite possible to combine the method with pulsed or FMCW methods, in order to be able to record the concentration distribution particularly precisely in a way that is easy and quick.

In another embodiment, a second microwave sensor, arranged offset with respect to the first microwave sensor in the circumferential direction of the channel and/or in the direction of flow of the gas flow through the channel, is used as the second microwave sensor. As a result, high precision may be realized with regard to the recording of the concentration distribution.

The choice of the frequency range of the at least one microwave sensor is completely free. However, a higher measuring resolution and an improved ratio of the measurement signal to signal noise may be realized by higher frequencies.

In another embodiment, a device is provided for determining at least one concentration of coal particles in a gas flow flowing through a channel. The device includes at least one microwave sensor for recording at least part of the gas flow with coal particles taken up therein and for providing at least one measurement signal characterizing the concentration of the coal particles. The device also includes an evaluation unit that is coupled with the microwave sensor and is designed to determine an autocorrelation function of the measurement signal and to determine at least one distance value characterizing a distance of a point of the gas flow associated with the concentration from the microwave sensor in dependence on the autocorrelation function. For example, the device is designed for carrying out the method of the embodiments discussed above.

The device not only makes possible the determination of the concentration, but also the determination of a position of the point at which the concentration is present (e.g., in relation to the gas flow or the channel as a whole). This allows the concentration distribution of the coal particles and also any inhomogeneities of the concentration distribution to be determined in a way that is particularly easy and involves little time and cost.

BRIEF DESCRIPTION OF THE DRAWINGS

FIG. 1 depicts a schematic view of a device for determining at least one concentration of coal particles in a gas flow flowing through a channel

DETAILED DESCRIPTION

FIG. 1 depicts a schematic view of a device for determining at least one concentration of coal particles in a gas flow flowing through a channel. The device includes at least one microwave sensor for providing a measurement signal and an evaluation unit designed to determine an autocorrelation function of the measurement signal and to determine at least one distance value characterizing a distance of a point of the gas flow associated with the concentration from the microwave sensor in dependence on the autocorrelation function.

In FIG. 1, a schematic cross-sectional view depicts a channel element in the form of a pipe 10 with a hollow cross section that is at least substantially circular and completely closed in the circumferential direction of the pipe 10 forming a channel 12. Channel 12 is bounded by the pipe 10. For example, the pipe 10 is a component of an internal combustion engine that has at least one combustion chamber.

A combustion process takes place in the combustion chamber. This combustion process is fed coal particles 14 that are taken up in a gas flow in the form of an air flow and are introduced into the combustion chamber by the air flow. As depicted in FIG. 1, upstream of the combustion chamber, the air flow with the coal particles 14 taken up therein flows through the channel 12.

In order to determine any inhomogeneities of the concentration distribution of the coal particles 14 in the air flow, a device 16 (denoted as a whole by numeral 16) for carrying out a method for determining at least one concentration of the coal particles 14 in the air flow is provided. The device 16 comprises at least two microwave sensors 18 and 20 that are arranged on a lateral surface 22 on the inner circumferential side of the pipe 10 in the channel 12 (e.g., bounding the channel 12). The device 16 also includes an evaluation unit 24, to which the microwave sensors 18 and 20 are connected. For recording the concentration, the microwave sensors 18 and 20 radiate microwaves in a respective recording areas 26 and 28. These microwaves are radiated into the channel 12, and consequently into the air flow with the coal particles 14 (e.g., as depicted in the recording areas 26 and 28). In this embodiment, the microwave sensors 18 and 20 are arranged offset in relation to one another in the circumferential direction of the channel 12, and the pipe 28, in such a way that the recording areas 26 and 28, or the respective center axes of the recording areas 26, form an included angle with one another. As a result, the recording areas 26 and 28 overlap one another in an overlapping area 30.

The microwave sensors 18 and 20 provide a respective measurement signal characterizing the concentration of the coal particles at least in the respective recording areas 26 and 28. It is possible based on the respective measurement signal to determine the respective concentration of the coal particles 14 in the respective measuring areas 26 and 28. Because the recording areas 26 and 28 overlap one another in the overlapping area 30, items of information about the concentration of the coal particles 14 in the overlapping area 30 are provided both by the microwave sensor 18 and by the microwave sensor 20. Both the measurement signal of the microwave sensor 18 and the measurement signal of the microwave sensor 20 contain a respective item of information about the concentration of the coal particles 14 in the overlapping area 30 such that the concentration of the coal particles 14 in the overlapping area 30 may be determined in dependence on the measurement signal of the microwave sensor 18 and in dependence on the measurement signal of the microwave sensor 20. These determined concentrations and measurement signals may be compared with one another so that any measuring errors can be compensated.

Thus, a concentration of the coal particles 14 at a point in the overlapping area 30 may be determined based on the measurement signal of the microwave sensor 18. The concentration of the coal particles 14 at this point may also be determined based on the measurement signal of the microwave sensor 20 because the recording areas 26 and 28 overlap one another. However, this point (e.g., the position of this point in relation to the pipe 20) is not yet known. In order to be able to record or determine the position of the point particularly precisely and easily, a respective autocorrelation function of the respective measurement signals is determined by the evaluation unit 24 and at least one respective distance value characterizing a distance of the point of the air flow associated with the concentration from the respective microwave sensor 18 and 20 is determined in dependence on the respective autocorrelation function. A first autocorrelation function of the measurement signal of the microwave sensor 18 is determined, while a first distance value that characterizes the distance of the point at which the concentration is present from the microwave sensor 18 is determined in dependence on the first autocorrelation function.

Further, a second autocorrelation function of the measurement signal of the microwave sensor 20 is determined. A second distance value that characterizes the distance of the point at which the concentration is present from the microwave sensor 20 is determined in dependence on the second autocorrelation function. Consequently, the distance of the point may be determined from the microwave sensor 18 and from the microwave sensor 20. From the distance information, the position of the point in relation to the channel 12 or the pipe 10 may finally be calculated. Consequently, the concentration of the coal particles 14 at the point is known, as well as the position of the point. In this way, for example, it is possible to determine the concentrations at different points in the air flow and the respective positions of these points. Further, the concentration distribution of the coal particles 14 in the air flow may be determined particularly easily such that any inhomogeneities of the concentration distribution can be recorded.

Further, using signal evaluation, it is possible to calculate and evaluate cross correlations or cross-correlation functions between the microwave sensors 18 and 20 and their measurement signals. With the aid of such cross correlations, for example, an imaging measuring method of the cross section of the pipe 10 may be provided.

By determining the distances with the aid of the autocorrelation functions, a microwave-based coal dust measurement with a very high spatial resolving capability may be realized in an easy way (e.g. with only little expenditure in terms of computation and circuitry).

The elements and features recited in the appended claims may be combined in different ways to produce new claims that likewise fall within the scope of the present invention. Thus, whereas the dependent claims appended below depend from only a single independent or dependent claim, it is to be understood that these dependent claims may, alternatively, be made to depend in the alternative from any preceding or following claim, whether independent or dependent. Such new combinations are to be understood as forming a part of the present specification.

While the present invention has been described above by reference to various embodiments, it should be understood that many changes and modifications can be made to the described embodiments. It is therefore intended that the foregoing description be regarded as illustrative rather than limiting, and that it be understood that all equivalents and/or combinations of embodiments are intended to be included in this description.

The invention claimed is:

1. A method for determining at least one concentration of coal particles in a gas flow flowing through a channel, the method comprising:
   recording using at least one microwave sensor at least part of the gas flow with coal particles taken up therein;
   providing at least one measurement signal characterizing the concentration of the coal particles;
   determining an autocorrelation function of the measurement signal; and
   characterizing at least one distance value for a distance to particles of the gas flow associated with the concentration from the microwave sensor in dependence on the autocorrelation function.

2. The method of claim 1, wherein the microwave sensor is operated with one frequency.

3. The method of claim 1, further comprising
   determining at least one position value that characterizes a position of the particles in relation to the channel in dependence on the distance value.

4. The method of claim 1, further comprising:
   recording, using a second microwave sensor, at least the part of the gas flow with the coal particles taken up therein;
   providing at least a second measurement signal characterizing the concentration of the coal particles;
   determining a second autocorrelation function of the second measurement signal; and characterizing at least a second distance value for a distance to the particles of the gas flow associated with the concentration from the second microwave sensor in dependence on the second autocorrelation function.

5. The method of claim 3, further comprising:
determining the position value in dependence on the distance values.

6. The method of claim 4, further comprising:
determining a cross-correlation function of the measurement signals of the first and second microwave sensors.

7. The method of claim 6, further comprising:
determining the position value in dependence on the cross-correlation function.

8. The method of claim 7, further comprising:
arranging the second microwave sensor offset with respect to the first microwave sensor in the circumferential direction of the channel;
arranging the second microwave sensor in the direction of flow of the gas flow through the channel; or
arranging the second microwave sensor offset with respect to the first microwave sensor in the circumferential direction of the channel and in the direction of flow of the gas flow through the channel.

9. A device for determining at least one concentration of coal particles in a gas flow flowing through a channel, the device comprising:
at least one microwave sensor configured to record at least part of the gas flow with coal particles taken up therein and configured to provide at least one measurement signal characterizing the concentration of the coal particles;
an evaluation unit coupled with the microwave sensor, the evaluation unit configured to determine an autocorrelation function of the measurement signal and configured to determine at least one distance value characterizing a distance to a point of the gas flow associated with the concentration from the microwave sensor in dependence on the autocorrelation function.

10. The device of claim 9, wherein the microwave sensor is operated with one frequency.

11. The device of claim 9, wherein the evaluation unit is configured to determine at least one position value that characterizes a position of the point in relation to the channel in dependence on the distance value.

12. The device of claim 11, wherein the evaluation unit is configured to determine the position value in dependence on the distance values.

13. The device of claim 9, further comprising:
a second microwave sensor configured to record at least the part of the gas flow with the coal particles taken up therein and configured to provide a second measurement signal characterizing the concentration of the coal particles;
wherein the evaluation unit is configured to determine a second autocorrelation function of the second measurement signal and to characterize at least a second distance value for a distance to the point of the gas flow associated with the concentration from the second microwave sensor in dependence on the second autocorrelation function.

14. The device of claim 13, wherein the evaluation unit is configured to determine a cross-correlation function of the measurement signals of the microwave sensors.

15. The device of claim 14, wherein the evaluation unit is configured to determine the position value in dependence on the cross-correlation function.

16. The device of claim 15, wherein
the second microwave sensor is arranged offset with respect to the first microwave sensor in the circumferential direction of the channel;
the second microwave sensor arranged in the direction of flow of the gas flow through the channel; or
the second microwave sensor arranged offset with respect to the first microwave sensor in the circumferential direction of the channel and in the direction of flow of the gas flow through the channel.

* * * * *